United States Patent [19]

Tacke et al.

[11] 4,237,137
[45] Dec. 2, 1980

[54] SILA-SUBSTITUTED 1,4-DIHYDROPYRIDINE DERIVATIVES AND THEIR MEDICINAL USE

[75] Inventors: Reinhold Tacke; Anke Bentlage, both of Braunschweig; Robertson Towart, Wuppertal; Wulf Vater, Leverkusen, all of Fed. Rep. of Germany

[73] Assignee: Bayer Aktiengesellschaft, Leverkusen, Fed. Rep. of Germany

[21] Appl. No.: 64,936

[22] Filed: Aug. 8, 1979

[30] Foreign Application Priority Data

Aug. 28, 1978 [DE] Fed. Rep. of Germany ....... 2837477

[51] Int. Cl.³ .................... C07D 403/04; A61K 31/44
[52] U.S. Cl. ...................................... 424/251; 546/14; 544/229; 424/258; 424/263
[58] Field of Search ................. 546/14, 321; 544/333, 544/229; 424/263, 251, 258

[56] References Cited

U.S. PATENT DOCUMENTS

| 3,905,983 | 9/1975 | Bossert et al. | 546/321 |
| 4,031,104 | 6/1977 | Bossert et al. | 546/321 |
| 4,044,141 | 8/1977 | Bossert et al. | 546/321 |

Primary Examiner—Henry R. Jiles
Assistant Examiner—Robert T. Bond
Attorney, Agent, or Firm—Sprung, Felfe, Horn, Lynch & Kramer

[57] ABSTRACT

The invention provides sila-substituted 1,4-dihydropyridine derivatives useful as medicament which influence the circulation. Also included in the invention are methods for the procurement of said derivatives, compositions containing said derivatives and methods for the use of said derivatives.

15 Claims, No Drawings

SILA-SUBSTITUTED 1,4-DIHYDROPYRIDINE DERIVATIVES AND THEIR MEDICINAL USE

The invention relates to new sila-substituted 1,4-dihydropyridine derivatives, several processes for their production and their use as medicaments which influence the circulation.

It has already been disclosed that 1,4-dihydropyridine derivatives possess valuable pharmacological properties (compare DT-OS (German Published Specification) No. 2,117,571 and F. Bossert et al., Naturwissenschaften 58, 578(1971)). Further, it is known that silicon also plays an important role biologically and, for example, occurs in the form of silicic acid esters, bonded to carbohydrates, steroids and fats, in the body of higher organisms (compare M. G. Voronkov et al., Silicium und Leben (Silicon and Life), Akademie-Verlag, Berlin 1975; G. Bendz and I. Lindquist (editors), Biochemistry of Silicon and Related Problems, Plenum Press, New York 1978). Silicon-containing 1,4-dihydropyridine derivatives have hitherto not been described.

The present invention relates to sila-substituted (e.g. silyl-alkyl-substituted) 1,4-dihydropyridine derivatives of the general formula $$R^3OOC\underset{R^4}{\overset{X}{\diagdown}}\underset{\underset{R}{|}}{\overset{H}{\diagup}}COOR^2 \qquad (I)$$

in which

R denotes a hydrogen atom or an alkyl or benzyl radical, $R^1$ and $R^4$ are identical or different and denote a hydrogen atom or an alkyl or trifluoromethyl radical and $R^2$ and $R^3$ are identical or different and denote a radical of the general formula $$-A-\underset{\underset{R^5}{|}}{\overset{\overset{R^7}{|}}{Si}}-R^6, \qquad (Ia)$$

in which

A denotes an optionally alkyl-substituted alkylene radical, and $R^5$, $R^6$ and $R^7$ are identical or different and each denotes an alkyl, cycloalkyl or phenyl radical, and these radicals are, in turn, optionally substituted by alkyl, alkoxy, halogen or trifluoromethyl, or one of the substituents $R^2$ or $R^3$ denotes a straight-chain or branched alkyl, cycloalkyl, alkenyl or alkinyl radical, and the alkyl radical, in turn, is optionally substituted by alkoxy or halogen, or by a phenyl radical which in turn optionally carries one, two or three substituents selected from trifluoromethyl, alkyl, alkoxy, halogen, nitro and alkylmercapto, or denotes an alkyl radical which is substituted by a group of the general formula $$-N\underset{R^9}{\overset{R^8}{\diagdown}}, \qquad (Ib)$$

in which $R^8$ and $R^9$ are identical or different and each denotes a hydrogen atom or an alkyl, aryl or aralkyl radical, and X denotes an alkyl, cycloalkyl, cycloalkenyl, aralkyl or aryl radical, and the aryl radical is optionally substituted by 1, 2 or 3 identical or different substituents selected from nitro, cyano, halogen, trifluoromethyl, amino, alkyl, alkoxy and trifluoromethoxy or by $SO_n$—alkyl (n is 0, 1 or 2), or denotes an optionally alkyl-, alkoxy- or halogen-substituted quinolyl, isoquinolyl, pyridyl, pyrimidyl, thienyl, furyl or pyrryl radical.

In the above definitions and unless otherwise specified in this specification, the terms "alkyl", "alkenyl", "alkinyl", "alkoxy", "alkylmercapto" and "alkylsulphonyl" refer to such groups having up to 7 carbon atoms; the term "cycloalkyl" refers to cycloalkyl having 3 to 7 ring carbon atoms, particularly 5 to 6 ring carbon atoms (e.g. cyclopropyl, cyclobutyl, cyclopentyl, cyclohexyl, cyclohepthl); the term "cycloalkenyl" refers to cycloalkenyl having 5 to 7, preferably 5 to 6 ring carbon atoms (e.g. cyclopentenyl, cyclohexenyl, cycloheptenyl, etc.) the term "halogen" refers particularly to fluorine, chlorine and bromine,; the term "aryl" refers preferably to mono- or bi-cyclic carbocyclic aryl having 6 to 10 carbon atoms, such as phenyl, bi-phenyl, naphthyl, etc.; and the term "aralkyl" refers to a group in which the aryl portion is defined as immediately above and the alkyl portion contains 1 to 4, preferably 1 to 2 carbon atoms.

It has been found that the compounds of the general formula I are obtained if (a) an aldehyde of the general formula $$X-CHO \qquad (II)$$

in which

X has the above-mentioned meaning is reacted with β-dicarbonyl compounds of the general formula $$R^2-O-\overset{\overset{O}{\|}}{C}-CH_2-\overset{\overset{O}{\|}}{C}-R^1 \qquad (III)$$

in which $R^1$ and $R^2$ have the above-mentioned meanings, and with an enamine of the general formula $$R^3-O-\overset{\overset{O}{\|}}{C}-CH=\overset{\overset{NHR}{|}}{C}-R^4 \qquad (IV)$$

in which R, $R^3$ and $R^4$ have the above-mentioned meanings, optionally in the presence of an inert organic solvent, at an elevated temperature, or (B) an ylidene compound of the general formula

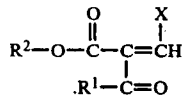

in which $R^1$, $R^2$ and X have the above-mentioned meanings, is reacted with an enamine of the above-mentioned formula (IV), optionally in the presence of an inert organic solvent, or (C) to prepare symmetrical sila-substituted 1,4-dihydropyridine derivatives, an aldehyde of the above-mentioned formula (II) is reacted with a two-fold molar amount of silicon-containing β-dicarbonyl compound of the formula (III) and with an amine derivative of the general formula

   (VI)

in which

R has the above-mentioned meaning, optionally in the presence of an inert organic solvents.

Remarkably, the sila-substituted 1,4-dihydropyridine derivatives according to the invention, of the general formula (I), exhibit powerful circulation-influencing effects. In particular, the compounds according to the invention inhibit the contractile properties of the smooth muscles of the vessels. They produce a distinct and long-lasting dilation of the coronary vessels and influence the heart metabolism in the sense of an energy saving. Furthermore, the compounds lower the blood pressure and can be used as anti-hypertensive agents. The vascular-spasmolytic effect of the sila-substituted 1,4-dihydropyridine derivatives can occur in the entire vascular system or manifest itself in an isolated manner in special vascular regions, such as, for example, in the peripheral region, in the coronary region or in the cerebral region.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution, e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

Examples of preferred excipients are water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol); solid excipients, such as, for example, natural rock powders (for example kaolins, aluminas, talc and chalk), synthetic rock powders (for example highly disperse silica and silicates) and sugars (for example sucrose, lactose and glucose); emulsifiers, such as non-ionic and anionic emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate), and in the case of oral use, the tablets preferably also contain, in addition to the excipients mentioned, preferred additives such as sodium citrate and calcium carbonate, together with various additional substances, such as starch, preferably potato starch and gelatine and optionally also lubricants, such as magnesium stearate, sodium lauryl-sulphate and talc.

All the pharmaceutical compositions according to the invention can also contain colouring agents and preservatives as well as perfumes and flavouring additions (e.g. peppermint oil and eucalyptus oil) and sweetening agents (.e.g saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for intravenous administration of the medicaments of the invention is 0.1 to 50 mg of active ingredient, and for oral administration is 25 to 500 mg of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), or rectally, preferably orally or parenterally, in particular perlingually or intravenously. Preferred pharmaceutical compositions and medicaments are therefore those adapted for administration such as oral or parenteral administration. Administration in the method of the invention is preferably oral or parenteral administration.

In general it has proved advantageous to administer intravenously amounts of from 0.001 mg to 10 mg/kg, preferably from 0.002 to 1 mg/kg, of body weight per day and to administer orally from 0.05 mg to 50 mg/kg, preferably from 0.5 to 10 mg/kg, of body weight per day, to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

Particular interest attaches to sila-substituted 1,4-dihydropyridine derivatives of the general formula (I), in which R denotes a hydrogen atom, an alkyl radical with 1 to 4 carbon atoms or a benzyl radical, $R^1$ and $R^4$ are identical or different and denote a hydrogen atom, an alkyl radical with 1 to 4 carbon atoms or a trifluoromethyl radical and $R^2$ and $R^3$ are identical or different and denote a radical of formula (Ia), in which A denotes an alkylene radical with 1 to 6 carbon atoms which is optionally substituted by alkyl with 1 to 4 carbon atoms and $R^5$, $R^6$ and $R^7$ are identical or different and each denotes an alkyl radical with 1 to 4 carbon atoms, a cycloalkyl radical with 3 to 7 carbon atoms or a phenyl radical, and these radicals are, in turn, optionally substituted by alkyl or alkoxy, each with 1 to 2 carbon atoms, halogen, especially fluorine, chlorine or bromine, or trifluoromethyl, or one of the substituents $R^2$ or $R^3$ denotes a straight-chain or branched alkyl, alkenyl or alkinyl radical or cycloalkyl radical, each with up to 6 carbon atoms, and the alkyl radical, in turn, is optionally substituted by alkoxy with 1 to 4 carbon atoms or by halogen, especially fluorine, chlorine or bromine, or by a phenyl radical which in turn can carry 1 or 2 substituents selected from trifluoromethyl, nitro, halogen, especially fluorine, chlorine and bromine, alkyl and alkoxy, each with 1 to 4 carbon atoms, or one of the substituents $R^2$ and $R^3$ denotes an alkyl radical with 1 to 4 carbon atoms, which is substituted by a radical of formula (Ib) in which $R^8$ and $R^9$ are identical or different and each denotes a hydrogen atom, an alkyl radical with 1 to 4 carbon atoms, or a phenyl or benzyl radical, and X denotes an alkyl radical with 1 to 4 carbon atoms, a cycloalkyl radical with 3 to 7 carbon atoms, a cycloalkenyl radical with 5 to 7 carbon atoms or a phenylalkyl radical with 1 to 3 carbon atoms in the alkyl chain, or a phenyl or naphthyl radical, and the phenyl radical is optionally substituted by 1, 2 or 3 identical or different substituents selected from nitro, cyano, halogen, especially fluorine, chlorine and bromine, trifluoromethyl, amino, trifluoromethoxy, alkyl, alkoxy, alkylmercapto and alkylsulphonyl, with 1 to 4 carbon atoms in each of the alkyl and alkoxy radicals mentioned, or denotes a quinolyl, isoquinolyl, pyridyl, pyrimidyl, thienyl, furyl or pyrryl radical which is optionally mono- or disubstituted by halogen, especially fluorine, chlorine or bromine, alkyl with 1 to 4 carbon atoms, or alkoxy with 1 to 4 carbon atoms. Compounds to be particularly singled out are new sila-substituted 1,4-dihydropyridine derivatives of the formula (I), in which R denotes a hydrogen atom or a methyl radical,
$R^1$ and $R^4$ denotes a methyl radical,
$R^2$ and $R^3$ have the preferred meanings given immediately above except that in the radical(s) of formula (Ia),
A denotes an optionally methyl-substituted alkylene radical with 1 to 6 carbon atoms, and
X denotes a phenyl or naphthyl radical, and the phenyl radical is optionally substituted by 1, 2 or 3 identical or different substituents selected from nitro, cyano, halogen, especially fluorine, chlorine and bromine, trifluoromethyl, amino, trifluoromethoxy, alkyl, alkoxy, alkylmercapto and alkylsulphonyl, each with 1 to 4 carbon atoms, or denotes a quinolyl, isoquinolyl, pyridyl, pyrimidyl, thienyl, furyl or pyrryl radical which is optionally substituted by halogen, especially fluorine, chlorine or bromine, alkyl with 1 to 4 carbon atoms or alkoxy with 1 to 4 carbon atoms. In carrying out the process according to the invention, the aldehydes of formula (II), employable as starting products, are known or can be prepared in accordance with known methods (E. Mosettig, Org. reactions VIII, 218 et. seq. (1954)).

The following may be mentioned as examples of aldehydes of formula (II);

2-, 3- or 4-Nitrobenzaldehyde, 2,4- or 2,6-dinitrobenzaldehyde, 2-nitro-6-bromobenzaldehyde, 2-nitro-3-methoxybenzaldehyde, 2- or 3-chlorobenzaldehyde, 3-trifluoromethylbenzaldehyde, 2-nitro-3-methoxy-6-chlorobenzaldehyde, 2-nitro-4-methoxybenzaldehyde, 3-nitro-6-chlorobenzaldehyde, 2-, 3- or 4-cyanobenzaldehyde, α-, β- or γ-pyridinaldehyde, 6-methylpyridin-2-aldehyde, pyrimidin-5-aldehyde, 4,6-dimethoxy-pyrimidin-5-aldehyde, 2-methoxymercaptobenzaldehyde, 2-methylsulphonylbenzaldehyde, 2-methylsulphinylbenzaldehyde, 1- or 2-naphthaldehyde, 5-bromo-1-naphthaldehyde, 2-ethoxy-1-naphthaldehyde, 4-methyl-1-naphthaldehyde, quinolin-2-, 3-, 4-, 5-, 6-, 7- or 8-aldehyde, isoquinolin-1- or 3-aldehyde, furan-2-aldehyde, thiophen-2-aldehyde and pyrrol-2-aldehyde.

The silicon-free and silicon-containing β-dicarbonyl compounds of the general formula III, employable according to the invention, are in some cases known, or can be prepared in accordance with known methods. The silicon-containing compounds of the general formula III can be prepared analogously to the silicon-free β-dicarbonyl compounds [V. F. Mironov, V. P. Kozyukov and V. D. Sheludyakov, Zh. Obsh. Khim. 37, 1,915 (1967)].

The following may be mentioned as examples of β-dicarbonyl compounds of formula (III);

Methyl acetoacetate, ethyl acetoacetate, propyl acetoacetate, propargyl acetoacetate, allyl acetoacetate, α- or β-methoxy-ethyl acetoacetate, α- or β-ethoxyethyl acetoacetate, ethyl formylacetate, cyclopentyl acetoacetate, neopentyl acetoacetate, 3,3-dimethyl-butyl acetoacetate, trimethylsilyl-methyl acetoacetate, 2-trimethylsilyl-ethyl acetoacetate, 3-trimethylsilyl-propyl acetoacetate, 2-triethylsilyl-ethyl acetoacetate, ethyldimethylsilyl-methyl acetoacetate, phenyldimethylsilylmethyl acetoacetate and p-fluorophenyldimethylsilylmethyl acetoacetate.

The silicon-free enamines, of formula (IV), employable according to the invention are already known or can be prepared in accordance with known methods. The silicon-containing enamines of formula (IV) were not previously known, but can be prepared analogously to the silicon-free enamines from the corresponding β-dicarbonyl compounds of the general formula (III) and amines of the general formula (VI). (A. C. Cope, J.A.C.S. 67, 1017 (1945)).

The following may be mentioned as examples of enamines of formula (IV);

Methyl β-aminocrotonate, ethyl β-aminocrotonate, propyl β-aminocrotonate, isopropyl β-aminocrotonate, neopentyl β-aminocrotonate, 3,3-dimethylbutyl β-aminocrotonate, trimethylsilyl-methyl β-aminocrotonate, triethylsilyl-methyl β-aminocrotonate, ethyldimethylsilylmethyl β-aminocrotonate and phenyldimethylsilylmethyl β-aminocrotonate.

The silicon-free ylidene compounds of formula (V), employable according to the invention, are already known or can be prepared in accordance with known methods. The silicon-containing ylidene compounds of formula (V), employable according to the invention, were on the other hand not previously known, but can be prepared analogously to the silicon-free compounds of formula (V) from aldehydes of formula (II) and from the corresponding β-dicarbonyl compounds of formula (III) by a Knovenagel condensation.

The following may be mentioned as examples of ylidene compounds of formula (V);

Methyl 2-(2-nitrobenzylidene)-acetoacetate, methyl 2-(3-nitrobenzylidene)-acetoacetate, methyl 2-(4-nitrobenzylidene)-acetoacetate, neopentyl 2-(3-nitrobenzylidene)-acetoacetate, 3,3-dimethylbutyl 2-(3-nitrobenzylidene)-acetoacetate, propin-2-yl 2-(3-nitrobenzylidene)-acetoacetate, isopropyl 2-(3-nitrobenzylidene)-acetoacetate, 2-methoxyethyl 2-(3-nitrobenzylidene)-acetoacetate, trimethylsilyl-methyl 2-(3-nitrobenzylidene)-acetoacetate, ethyldimethyl 2-(3-nitrobenzylidene)-acetoacetate and trimethylsilyl-methyl 2-(3-chlorobenzylidene)-acetoacetate.

The amine derivatives of formula (VI), employable according to the invention, are already known; the following may be mentioned as examples;

Ammonia, methylamine, ethylamine, propylamine, isopropylamine, butylamine, isobutylamine and benzylamine.

Suitable diluents are water and all inert organic solvents. These preferentially include alcohols, such as ethanol and methanol, ethers, such as dioxane and diethyl ether, or glacial acetic acid, dimethylformamide, dimethylsulphoxide, acetonitrile and the like.

The reaction temperatures can be varied within a substantial range. In general, the reaction is carried out at 80°–90° C. The preferred embodiment consists in carrying out the reactions in boiling ethanol.

The reaction can be carried out under normal pressure but also under elevated pressure. In general, it is carried out under normal pressure.

In carrying out the process variants according to the invention, the materials participating in the reaction are each employed in approximately stoichiometric amounts. The amine used, of the formula (VI), or a salt thereof, is preferably added in excess (1.5–2 times the molar amount).

The following may be mentioned individually as new active compounds of the present invention: 2,6-dimethyl-4-(2-nitrophenyl)-1,4-dihydropyridine-3,5-dicarboxylic acid 3-ethyl ester 5-(trimethylsilyl-methyl) ester, 2,6-dimethyl-4-(3-nitrophenyl)-1,4-dihydropyridine-3,5-dicarboxylic acid 3-ethyl ester 5-(trimethylsilyl-methyl) ester, 2,6-dimethyl-4-(2-nitrophenyl)-1,4-dihydropyridine-3,5-dicarboxylic acid 3-methyl ester 5-(2-trimethylsilyl-ethyl) ester, 2,6-dimethyl-4-(3-nitrophenyl)-1,4-dihydropyridine-3,5-dicarboxylic acid 3-methyl ester 5-(2-trimethylsilyl-ethyl) ester, 2,6-dimethyl-4-(4-nitrophenyl)-1,4-dihydropyridine-3,5-dicarboxylic acid 3-methyl ester 5-(2-trimethylsilyl-ethyl) ester, 2,6-dimethyl-4-(2-nitrophenyl)-1,4-dihydropyridine-3,5-dicarboxylic acid 3-methyl ester 5-(dimethylphenylsilyl-methyl) ester, 2,6-dimethyl-4-(3-nitrophenyl)-1,4-dihydropyridine-3,5-dicarboxylic acid 3-methyl ester 5-(dimethylphenylsilyl-methyl) ester, 2,6-dimethyl-4-(2-chlorophenyl)-1,4-dihydropyridine-3,5-dicarboxylic acid 3-methyl ester 5-(dimethylphenylsilylmethyl) ester, 2,6-dimethyl-4-(3-nitrophenyl)-1,4-dihydropyridine-3,5-dicarboxylic acid 3-(trimethylsilyl-methyl) ester 5-(2-trimethylsilyl-ethyl) ester, 2,6-dimethyl-4-(2-chlorophenyl)-1,4-dihydropyridine-3,5-dicarboxylic acid 3-methyl ester 5-(trimethylsilyl-methyl) ester, 1,2,6-trimethyl-4-(2-nitrophenyl)-1,4-dihydropyridine-3,5-dicarboxylic acid 3-methyl ester 5-(trimethylsilyl-methyl) ester and 1,2,6-trimethyl-4-(3-nitrophenyl)-1,4-dihydropyridine-3,5-dicarboxylic acid 3-methyl ester 5-(trimethylsilyl-methyl) ester.

The preparation of compounds according to the present invention will now be illustrated in the following Examples.

EXAMPLE 1

(a)

2,6-Dimethyl-4-(3-nitrophenyl)-1,4-dihydropyridine-3,5-dicarboxylic acid bis-(trimethylsilyl-methyl)ester 18.2 g of trimethylsilyl-methyl acetoacetate, 7.3 g of 3-nitrobenzaldehyde and 5.5 ml of concentrated ammonia, in 30 ml of 96 percent strength ethanol, are heated to the boil for 20 hours. After cooling, the product is filtered off and dried, and 16.9 g of yellow crystals of melting point 159° C. (ethanol) are obtained.

In the same way, the following are obtained, after 20 hours' boiling in 20 ml of 96 percent strength ethanol, from 11.3 g of trimethylsilyl-methyl acetoacetate, 3.3 ml of concentrated ammonia (b) and 4.5 g of 2-nitrobenzaldehyde: 8.1 g of 2,6-dimethyl-4-(2-nitrophenyl)-1,4-dihydropyridine-3,5-dicarboxylic acid bis-(trimethylsilyl-methyl) ester, melting point 157° C. (ethanol).

(c) and 3.18 g of benzaldehyde: 6.2 g og 2,6-dimethyl-4-phenyl-1,4-dihydropyridine-3,5-dicarboxylic acid bis-(trimethylsilyl-methyl) ester, melting point 123° C. (ether/petroleum ether).

(d) and 4.22 g of 3-chlorobenzaldehyde: 6.7 g of 2,6-dimethyl-4-(3-chlorophenyl)-1,4-dihydropyridine-3,5-dicarboxylic acid bis-(trimethylsilyl-methyl) ester, meltingpoint 129° C. (ether/petroleum ether).

(e) and 4.22 g of 2-chlorobenzaldehyde: 6.9 g of 2,6-dimethyl-4-(2-chlorophonyl)-1,4-dihydropyridine-3,5-dicarboxylic acid bis-(trimethylsilyl-methyl) ester, melting point 128° C. (ether/petroleum ether).

(f) and 3.21 g of pyridin-3-aldehyde: 11.3 g of 2,6-dimethyl-4-(3-pyridyl)-1,4-dihydropyridine-3,5-dicarboxylic acid bis-(trimethylsilyl-methyl) ester, melting point 149° C. (ethanol/ether).

(g) and 3.21 g of pyridin-2-aldehyde: 8.1 g of 2,6-dimethyl-4-(2-pyridyl)-1,4-dihydropyridine-3,5-dicarboxylic acid bis-(trimethylsilyl-methyl) ester, melting point 203° C. (ethanol/methanol).

EXAMPLE 2

2,6-Dimethyl-4-(3-nitrophenyl)-1,4-dihydropyridine-3,5-dicarboxylic acid bis-(dimethylphenylsilyl-methyl) ester 10.0 g of dimethylphenylsilylmethyl acetoacetate, 3.0 g of 3-nitrobenzaldehyde and 2.2 ml of concentrated ammonia in 15 ml of 96 percent strength ethanol are heated under reflux for 20 hours. After cooling and filtering, 11.0 g of yellow crystals of melting point 125° C. (ethanol) are obtained.

EXAMPLE 3

2,6-Dimethyl-4-(3-nitrophenyl)-1,4-dihydropyridine-3,5-dicarboxylic acid bis-(2-trimethylsilyl-ethyl) ester After boiling 5.0 g of 2-trimethylsilylethyl acetoacetate, 1.9 g of 3-nitrobenzaldehyde and 1.5 ml of concentrated ammonia in 10 ml of 96 percent strength ethanol for 20 hours, then cooling and filtering off the product, 3.5 g of pale yellow crystals of melting point 120° C. (ethanol) are obtained.

EXAMPLE 4

2,6-Dimethyl-4-(3-nitrophenyl)-1,4-dihydropyridine-3,5-dicarboxylic acid 3-neopentyl ester 5-trimethylsilyl-methyl ester After heating 5.6 g of trimethylsilyl-methyl β-aminocrotonate, 5.2 g of neopentyl acetoacetate and 4.5 g of 3-nitrobenzaldehyde in 20 ml of 96 percent strength ethanol for 17 hours, the mixture is allowed to cool, the product is filtered off and 10.4 g of yellow crystals of melting point 176° C. (ethanol) are obtained.

EXAMPLE 5

(a)

2,6-Dimethyl-4-(2-nitrophenyl)-1,4-dihydropyridine-3,5-dicarboxylic acid 3-methyl ester 5-trimethylsilyl-methyl ester 6.44 g of methyl 2-(2-nitrobenzylidene)-acetoacetate and 4.84 g of trimethylsilyl-methyl β-aminocrotonate in 17 ml of 96 percent strength ethanol are heated under reflux for 20 hours. The solvent is then stripped off in vacuo and the residue is crystallised from ethanol/ether (1:1). 7.5 g of deep yellow crystals of melting point 156° C. (ethanol/ether) are obtained.

In the same manner, the following are obtained, after 20 hours' boiling in 20 ml of 96 percent strength ethanol, from 5.62 g of trimethylsilyl-methyl β-aminocrotonate (b) and 7.48 g of methyl 2-(3-nitrobenzylidene)-acetoacetate: 10.6 g of 2,6-dimethyl-4-(3-nitrophenyl)-1,4-dihydropyridine-3,5-dicarboxylic acid 3-methyl ester 5-trimethylsilyl-methyl ester, melting point 120° C. (ether/petroleum ether).

(c) and 7.48 g of methyl 2-(4-nitrobenzylidene)-acetoacetate: 11.3 g of 2,6-dimethyl-4-(4-nitrophenyl)-1,4-dihydropyridine-3,5-dicarboxylic acid 3-methyl ester 5-trimethylsilyl-methyl ester, melting point 137° C. (methanol).

EXAMPLE 6

2,6-Dimethyl-4-(3-nitrophenyl)-1,4-dihydropyridine-3,5-dicarboxylic acid 3-propin-2-yl ester 5-trimethylsilyl-methyl ester After heating 5.62 g of trimethylsilyl-methyl $\beta$-aminocrotonate, 8.20 g of propin-2-yl 2-(3-nitrobenzylidene)-acetoacetate and 20 ml of 96 percent strength ethanol for 20 hours, the mixture is allowed to cool and 14.25 g of pale yellow crystals are obtained. Melting point 148° C. (ethanol).

EXAMPLE 7

2,6-Dimethyl-4-(3-nitrophenyl)-1,4-dihydropyridine-3,5-dicarboxylic acid 3-isopropyl ester 5-trimethylsilyl-methyl ester 8.32 g of isopropyl 2-(3-nitrobenzylidene)-acetoacetate and 5.62 g of trimethylsilyl-methyl $\beta$-aminocrotonate are heated for 20 hours in 20 ml of 96 percent strength ethanol, the mixture is allowed to cool and 11.8 g of yellow crystals of melting point 121° C. (ethanol/ether) are obtained.

EXAMPLE 8

2,6-Dimethyl-4-(3-nitrophenyl)-1,4-dihydropyridine-3,5-dicarboxylic acid 3-(2-methoxyethyl) ester 5-trimethylsilyl-methyl ester 8.80 g of 2-methoxyethyl 2-(3-nitrobenzylidene)acetoacetate and 5.62 g of trimethylsilyl-methyl $\beta$-aminocrotonate are heated under reflux in 20 ml of 96 percent strength ethanol for 20 hours. The solvent is then stripped off and the residue is crystallised from ether/petroleum ether (1:1). Filtration gives 11.5 g of yellow crystals of melting point 92° C. (ether/petroleum).

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

What is claimed is:

1. A compound of the formula $$R^3OOC \underset{R_4}{\overset{X}{\underset{\underset{R}{\overset{|}{N}}}{\bigwedge}}} \overset{H}{\underset{R^1}{\overset{COOR^2}{\bigwedge}}} \quad (I)$$

in which

R denotes a hydrogen atom or an alkyl or benzyl radical, $R^1$ and $R^4$ are identical or different and denote a hydrogen atom or an alkyl or trifluoromethyl radical and $R^2$ and $R^3$ are identical or different and denote a radical of the general formula $$-A-\underset{\underset{R^5}{\overset{|}{\mid}}}{\overset{R^7}{\overset{|}{Si}}}-R^6, \quad (Ia)$$

in which

A denotes an optionally $C_1$-$C_4$-alkyl-substituted $C_1$-$C_6$-alkylene radical and $R^5$, $R^6$ and $R^7$ are identical or different and each denotes an alkyl, cycloalkyl or phenyl radical, and these radicals are, in turn, optionally substituted by alkyl, alkoxy, halogen or trifluoromethyl, or one of the substituents $R^2$ or $R^3$ denotes a straight-chain or branched alkyl, cycloalkyl, alkenyl or alkynyl radical, and the alkyl radical, in turn, is optionally substituted by alkoxy or halogen, or by a phenyl radical which in turn optionally carries one or more substituents selected from trifluoromethyl, alkyl, alkoxy, halogen, nitro and alkylmercapto, or denotes an alkyl radical which is substituted by a group of the general formula $$-N\underset{R^9}{\overset{R^8}{\diagdown}} , \quad (Ib)$$

in which $R^8$ and $R^9$ are identical or different and each denote a hydrogen atom or an alkyl, aryl or aralkyl radical, and X denotes an alkyl, cycloalkyl, cycloalkenyl, aralkyl or aryl, and the aryl radical is optionally substituted by 1, 2 or 3 identical or different substituents selected from nitro, cyano, halogen, trifluoromethyl, amino, alkyl, alkoxy, and trifluoromethoxy or by $SO_n$-alkyl (n is 0, 1 or 2), or denotes an optionally alkyl-, alkoxy- or halogen-substituted quinolyl, isoquinolyl, pyridyl, pyrimidyl, thienyl, furyl or pyrryl radical, each of said alkyl, alkenyl, alkynyl, alkoxy, alkylmercapto and alkylsulphonyl groups having up to 7 carbon atoms, each of said cycloalkyl groups having 3 to 7 ring carbon atoms, each of said cycloalkenyl groups having 5 to 7 ring carbon atoms, each aryl group being mono- or bi-cyclic carbocyclic aryl having 6 to 10 carbon atoms and each aralkyl group being mono- or bi-cyclic carbocylic aryl having 6 to 10 carbon atoms in the aryl portion and 1 to 4 carbon atoms in the alkyl portion.

2. A compound according to claim 1, in which

R denotes a hydrogen atom, an alkyl radical with 1 to 4 carbon atoms or a benzyl radical, $R^1$ and $R^4$ are identical or different and denote a hydrogen atom, an alkyl radical with 1 to 4 carbon atoms or a trifluoromethyl radical and $R^2$ and $R^3$ are identical or different and denote a compound of formula (Ia) as described in claim 1, in which A denotes an alkylene radical with 1 to 6 carbon atoms which is optionally substituted by alkyl with 1 to 4 carbon atoms and $R^5$, $R^6$ and $R^7$ are identical or different and each denotes an alkyl radical with 1 to 4 carbon atoms, a cycloalkyl radical with 3 to 7 carbon atoms or a phenyl radical, and these radicals are, in turn, optionally substituted by alkyl or alkoxy, each with 1 to 2 carbon atoms, halogen or trifluoromethyl, or one of the substituents $R^2$ or $R^3$ denotes a straight-chain or branched alkyl, alkenyl or alkynyl radical or cycloalkyl radical, each with up to 6 carbon atoms, and the alkyl radical, in turn, is optionally substituted by alkoxy with 1 to 4 carbon atoms or by halogen, or by a phenyl radical which in turn can carry 1 or 2 substituents selected from trifluoromethyl, nitro, halogen, and alkyl and alkoxy, each with 1 to 4 carbon atoms, or one of the substituents $R^2$ and $R^3$ denotes an alkyl radical with 1 to 4 carbon atoms, which is substituted by a radical of formula (Ib) as described in claim 1, in which $R^8$ and $R^9$ are identical or different and each denote a hydrogen atom or an alkyl radical with 1 to 4 carbon atoms, or a phenyl or benzyl radical, and X denotes an alkyl radical with 1 to 4 carbon atoms, a cycloalkyl radical with 3 to 7 carbon atoms, a cycloalkenyl radical with 5 to 7 carbon atoms or a phenylalkyl radical with 1 to 3 carbon atoms in the alkyl chain or a phenyl or naphthyl radical, and the phenyl radical is optionally substituted by 1, 2 or 3 identical or different substituents selected from nitro, cyano, halogen, trifluoromethyl, amino, trifluoromethoxy, alkyl, alkoxy, alkylmercapto and alkylsulphonyl, with 1 to 4 carbon atoms in each of the alkyl and alkoxy radicals mentioned, or denotes a quinolyl, isoquinolyl, pyridyl, pyrimidyl, thienyl, furyl or pyrryl radical which is optionally substituted by halogen, alkyl with 1 to 4 carbon atoms, or alkoxy with 1 to 4 carbon atoms.

3. A compound according to claim 2, in which R denotes a hydrogen atom or a methyl radical, $R^1$ and $R^4$ denote methyl radicals, $R^2$ and $R^3$ have the same meanings as in claim 2 except that in the radical(s) of formula (Ia) as described in claim 1 A denotes an optionally methyl-substituted alkylene radical with 1 to 6 carbon atoms and X denotes a phenyl or naphthyl radical, and the phenyl radical is optionally substituted by 1, 2 or 3 identical or different substituents selected from nitro, cyano, halogen, trifluoromethyl, amino, trifluoromethoxy, alkyl, alkoxy, alkylmercapto and alkylsulphonyl, each with 1 to 4 carbon atoms, or denotes a quinolyl, isoquinolyl, pyridyl, pyrimidyl, thienyl, furyl or pyrryl radical which is optionally substituted by halogen, alkyl with 1 to 4 carbon atoms or alkoxy with 1 to 4 carbon atoms.

4. A pharmaceutical composition containing as an active ingredient an amount effective for treatment of circulatory diseases of a compound according to claim 1 in admixture with an inert pharmaceutical carrier.

5. A pharmaceutical composition of claim 4 in the form of a sterile or physiologically isotonic aqueous solution.

6. A composition according to claim 4 or 5 containing from 0.5 to 90% by weight of the said active ingredient.

7. A medicament of claim 4 in the form of tablets, pills, dragees, capsules, ampoules, or suppositories.

8. A method of combating circulatory diseases in warm-blooded animals which comprises administering to the said animals an active compound according to claim 1 either alone or in admixture with a diluent or in the form of a medicament.

9. A method according to claim 8 in which the active compound is administered intravenously in an amount of 0.001 to 10 mg per kg body weight per day.

10. A method according to claim 9 in which the active compound is administered intravenously in an amount of 0.002 to 1 mg per kg body weight per day.

11. A method according to claim 8 in which the active compound is administered orally in an amount of 0.05 to 50 mg per kg body weight per day.

12. A method according to claim 11 in which the active compound is administered orally in an amount of 0.5 to 10 mg per kg body weight.

13. A compound according to claim 1, which is 2,6-Dimethyl-4-(3-nitrophenyl)-1,4-dihydropyridine-3,5-dicarboxylic acid bis-(trimethylsilyl-methyl) ester.

14. A compound according to claim 1, which is 2,6-Dimethyl-4-(2-nitrophenyl)1,4-dihydropyridine-3,5-dicarboxylic acid 3-methyl ester 5-trimethylsily-methyl ester 15. A compound according to claim 1, which is 2,6-Dimethyl-4-(3-nitrophenyl)-1,4-dihydropyridine-3,5-dicarboxylic acid 3-isopropyl ester 5-trimethylsilyl-methyl ester.

* * * * *